United States Patent
Whelan

(10) Patent No.: US 11,759,213 B2
(45) Date of Patent: Sep. 19, 2023

(54) TOURNIQUET CLIP

(71) Applicant: Chris Whelan, Huntington Beach, CA (US)

(72) Inventor: Chris Whelan, Huntington Beach, CA (US)

(73) Assignee: NOBLE HOUSE GROUP PTY. LTD.

( * ) Notice: Subject to any disclaimer, the term of this patent is extended or adjusted under 35 U.S.C. 154(b) by 812 days.

(21) Appl. No.: 16/760,455

(22) PCT Filed: Oct. 31, 2018

(86) PCT No.: PCT/AU2018/051180
§ 371 (c)(1),
(2) Date: Apr. 30, 2020

(87) PCT Pub. No.: WO2019/084614
PCT Pub. Date: May 9, 2019

(65) Prior Publication Data
US 2020/0289131 A1  Sep. 17, 2020

Related U.S. Application Data

(60) Provisional application No. 62/579,165, filed on Oct. 31, 2017.

(51) Int. Cl.
  A61B 17/132 (2006.01)
  A44B 11/06 (2006.01)
  A44B 11/25 (2006.01)

(52) U.S. Cl.
  CPC ........ *A61B 17/1327* (2013.01); *A44B 11/065* (2013.01); *A44B 11/2592* (2013.01)

(58) Field of Classification Search
  CPC .............. A61B 17/132; A61B 17/1322; A61B 17/1327; A44B 11/06; A44B 11/065; A44B 11/2592
  See application file for complete search history.

(56) References Cited

U.S. PATENT DOCUMENTS 3,818,548 A * 6/1974 Meyerson .............. A44B 11/06
                                                       24/191
4,387,489 A   6/1983 Dudek
(Continued)

FOREIGN PATENT DOCUMENTS

DE    3602778    8/1987
EP    0513485    11/1992
(Continued)

*Primary Examiner* — Ryan J. Severson
(74) *Attorney, Agent, or Firm* — Galbreath Law Offices, P.C.; John A. Galbreath

(57) ABSTRACT

A clip adapted for use with an elongate strap for forming a tourniquet including first and second parts adapted to be connected to the strap, the first and second parts adapted to be releasably connected together to form a closed loop. The second part is adapted to movable along the strap and has an open passageway through which the strap passes. Integrally formed first and second elongate walls define at least part of the passageway and first and second grip portions for gripping the strap. The second wall is mounted for rotation about a transverse axis so as to move the grip portion of the second wall toward or away from the first grip portion.

20 Claims, 14 Drawing Sheets

(56) References Cited

U.S. PATENT DOCUMENTS

| | | | | |
|---|---|---|---|---|
| 4,633,549 | A * | 1/1987 | Lovato | E05B 65/5284 |
| | | | | 24/615 |
| 5,084,062 | A * | 1/1992 | Sturm | A61B 17/1327 |
| | | | | 24/168 |
| 5,535,485 | A | 7/1996 | Kirchner | |
| 6,217,601 | B1 * | 4/2001 | Chao | A61B 17/1327 |
| | | | | 606/203 |
| 6,510,592 | B1 * | 1/2003 | Hamilton | A44B 11/06 |
| | | | | 24/3.1 |
| 6,678,925 | B1 * | 1/2004 | Howell | A44B 11/2592 |
| | | | | 24/647 |
| 7,171,729 | B2 * | 2/2007 | Bulanda | F16L 3/233 |
| | | | | 24/23 R |
| 10,136,903 | B2 * | 11/2018 | Lynch | A61B 17/1732 |
| 10,993,726 | B2 * | 5/2021 | Karvandi | A61H 11/00 |
| 11,298,139 | B2 * | 4/2022 | Voros | A61B 17/1327 |
| 2005/0120520 | A1 * | 6/2005 | Bulanda | F16L 3/233 |
| | | | | 24/16 R |
| 2007/0193004 | A1 * | 8/2007 | Chou | A44B 11/06 |
| | | | | 24/170 |
| 2017/0273694 | A1 * | 9/2017 | Lynch | G16H 20/40 |
| 2019/0076153 | A1 * | 3/2019 | Karvandi | A63B 21/00047 |
| 2020/0237379 | A1 * | 7/2020 | Voros | A61B 17/1327 |
| 2020/0289131 | A1 * | 9/2020 | Whelan | A44B 11/2592 |
| 2023/0100046 | A1 * | 3/2023 | Pontaoe | A44B 11/2592 |
| | | | | 24/614 |

FOREIGN PATENT DOCUMENTS

| | | |
|---|---|---|
| EP | 0374464 | 6/1995 |
| GB | 2138490 | 10/1986 |

* cited by examiner

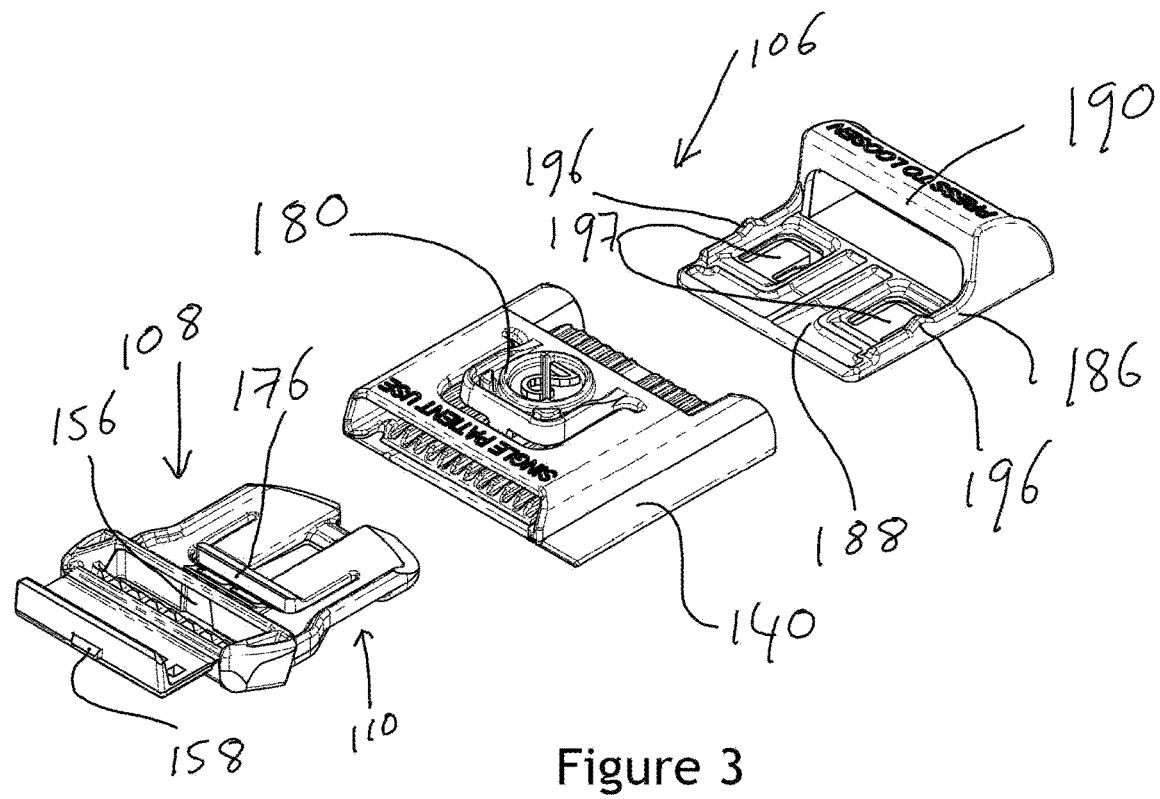
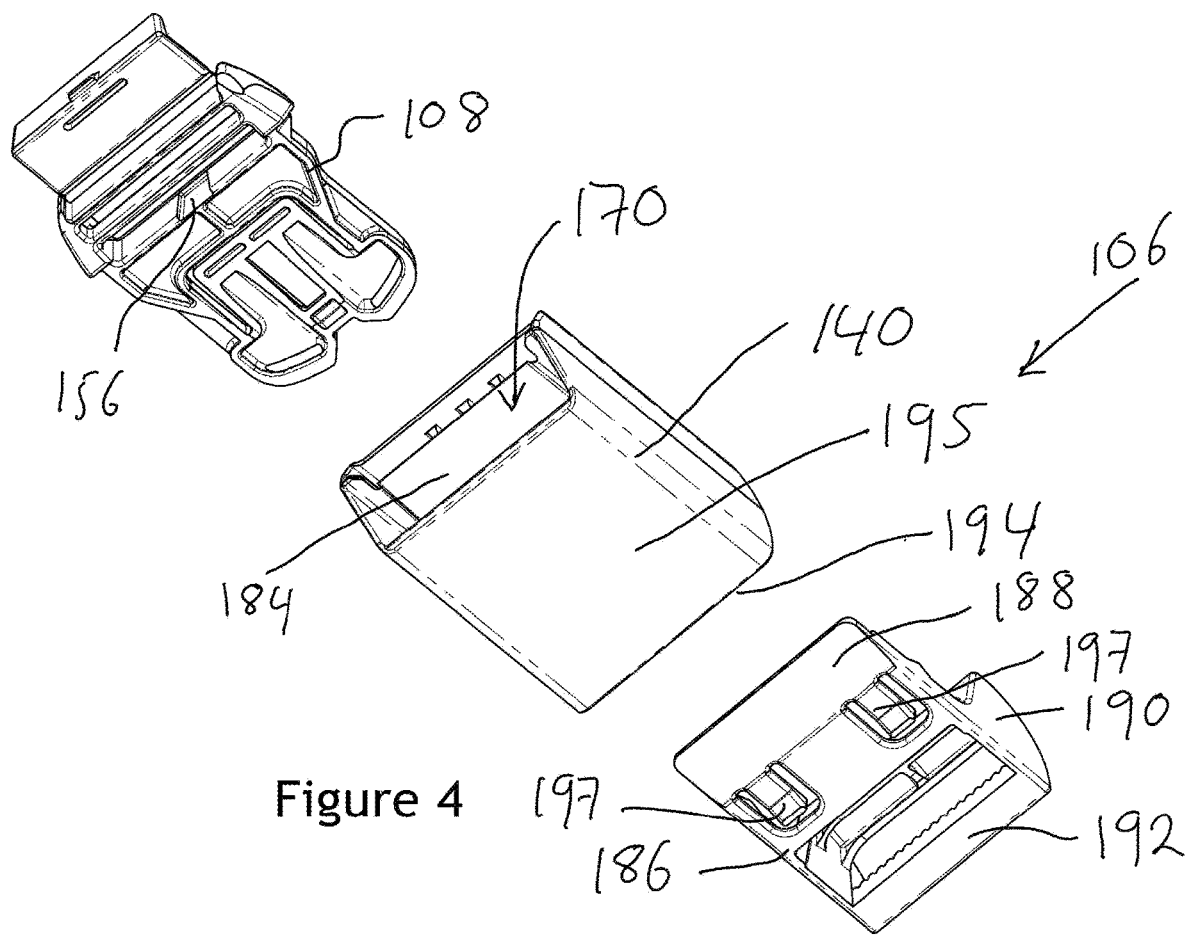
Figure 3
Figure 4

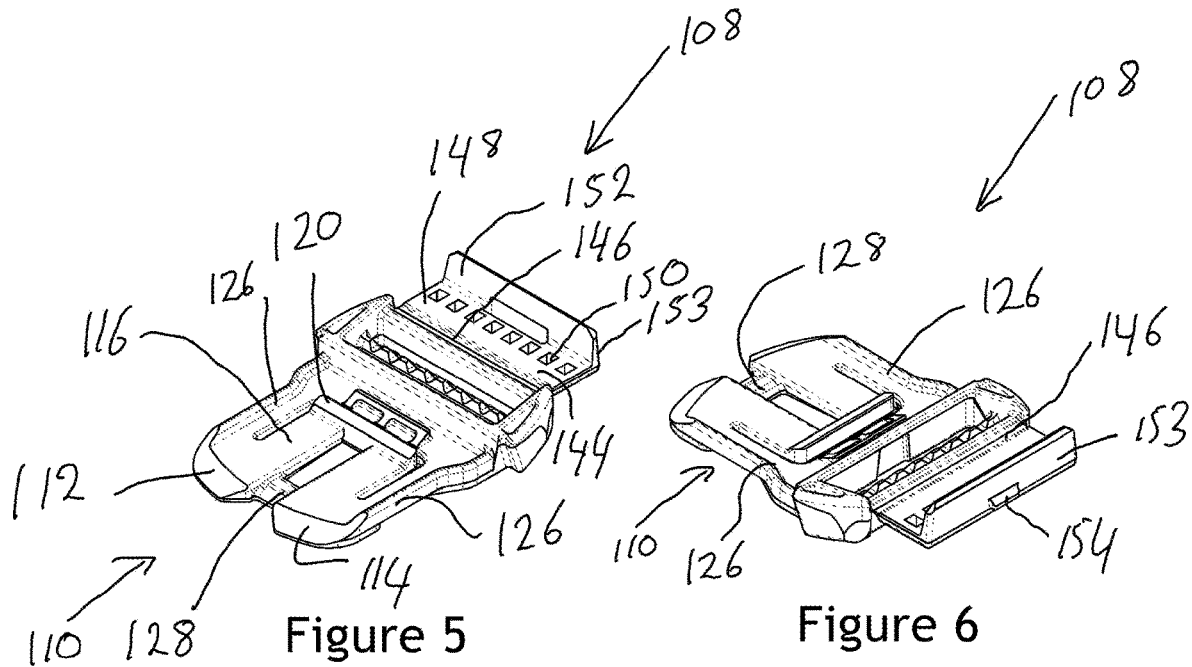
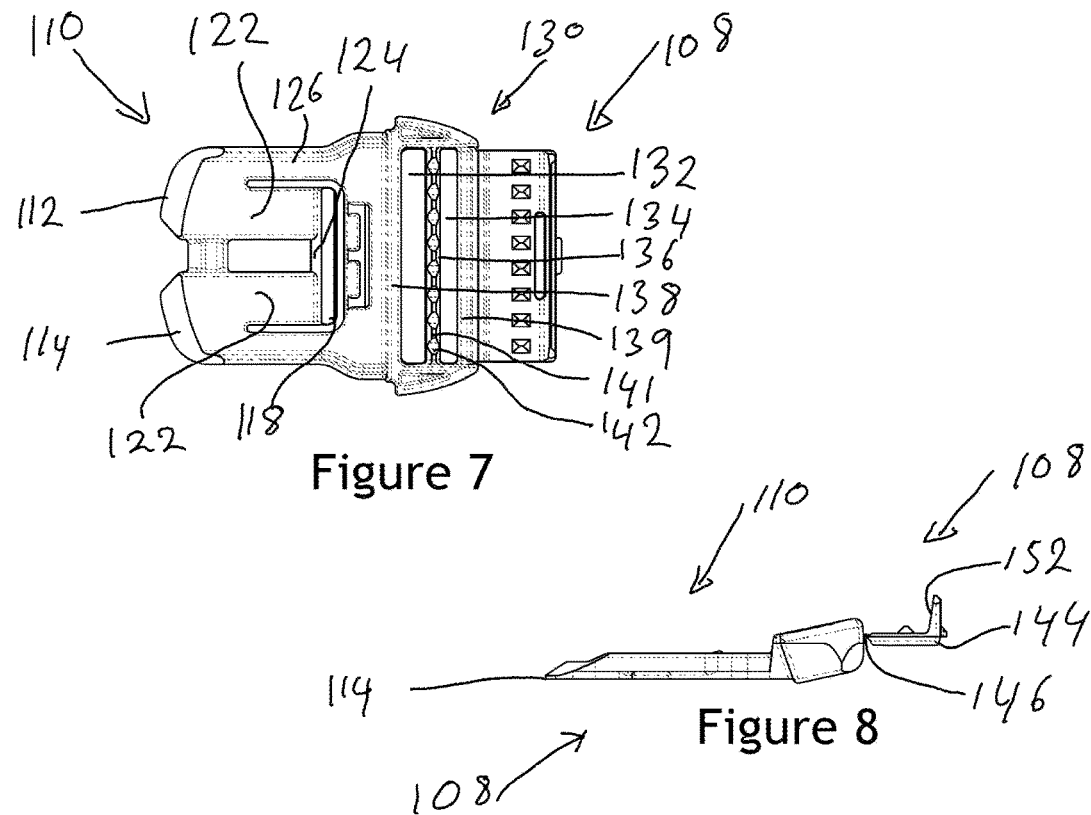

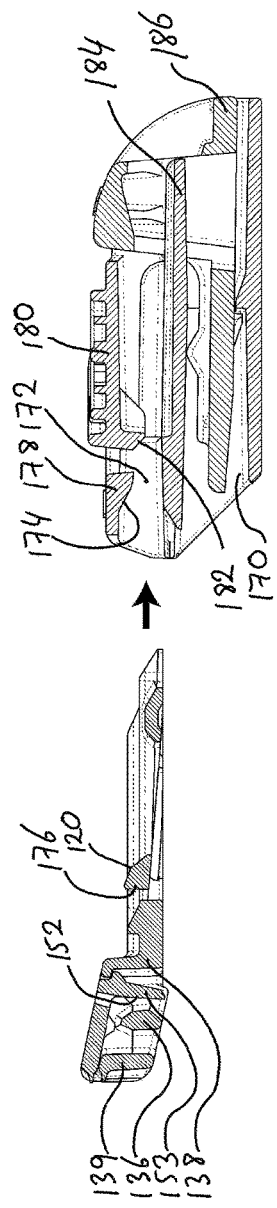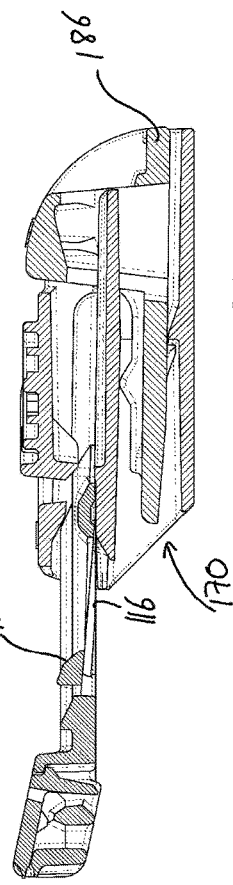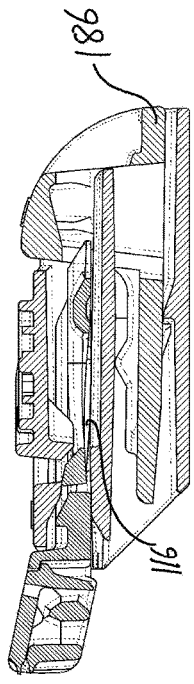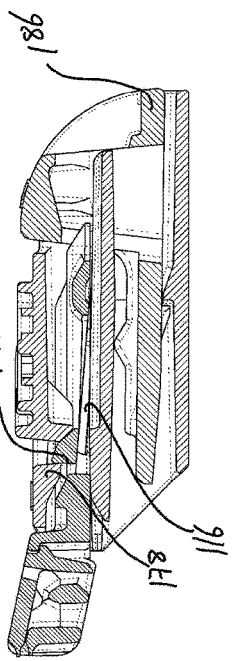

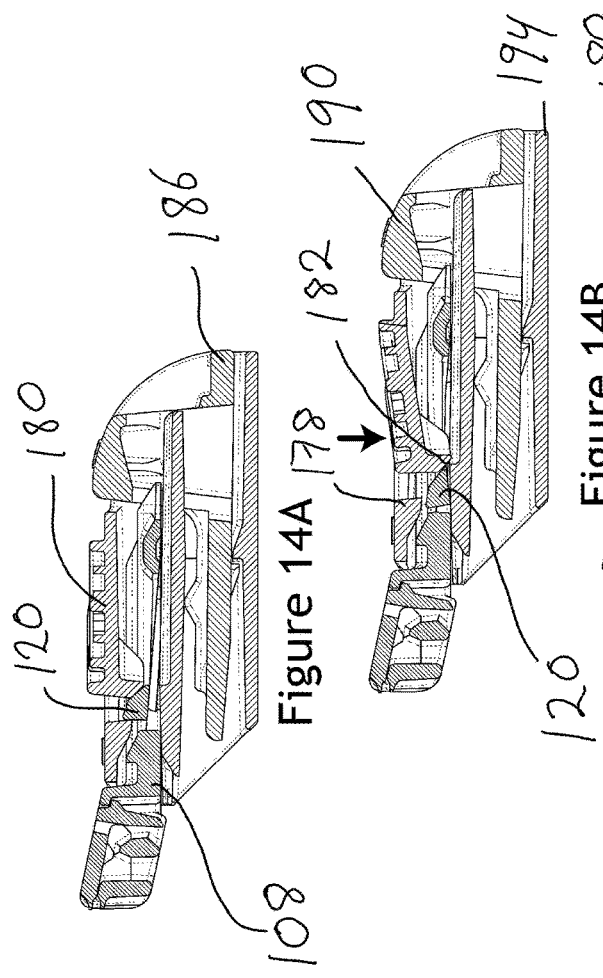

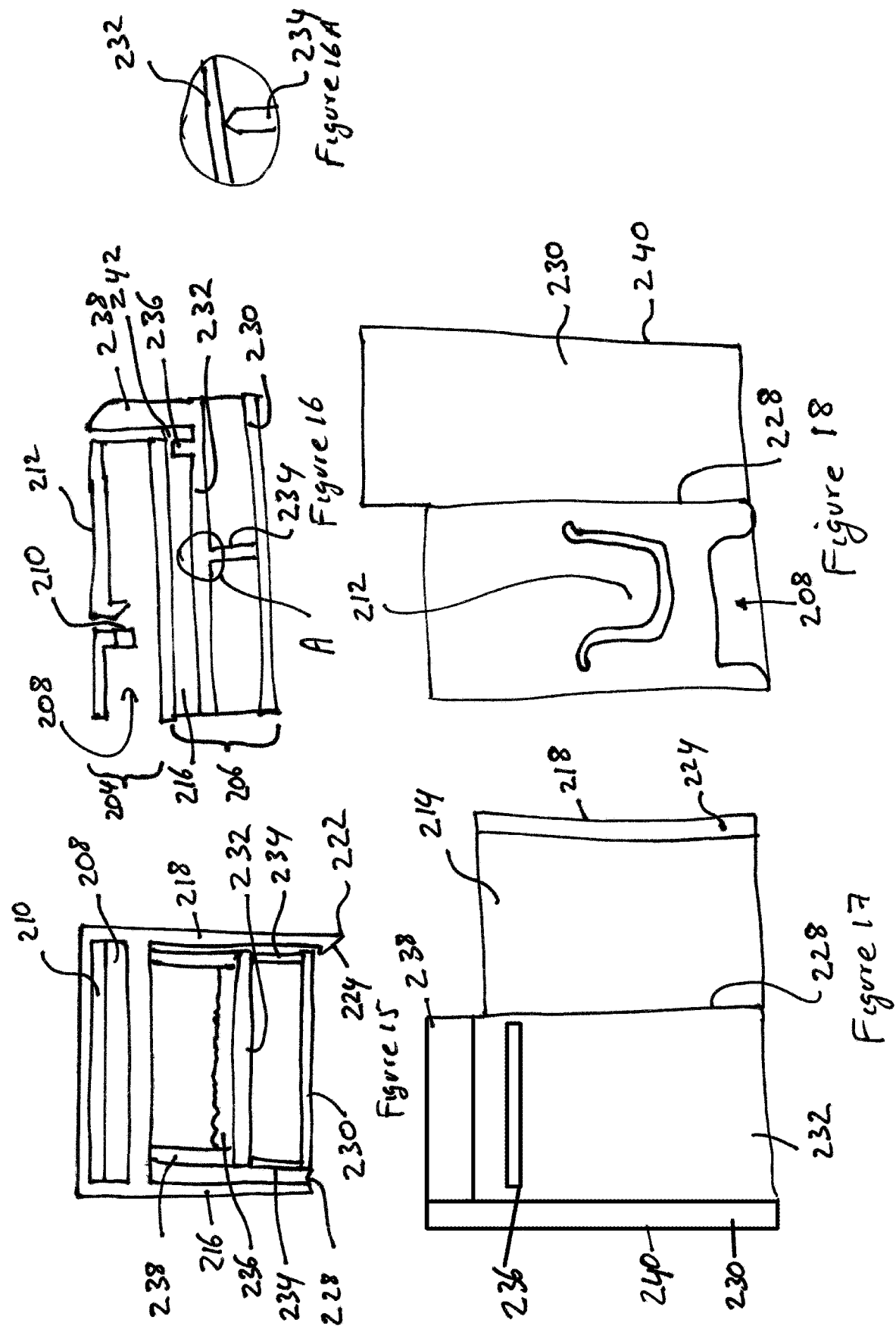

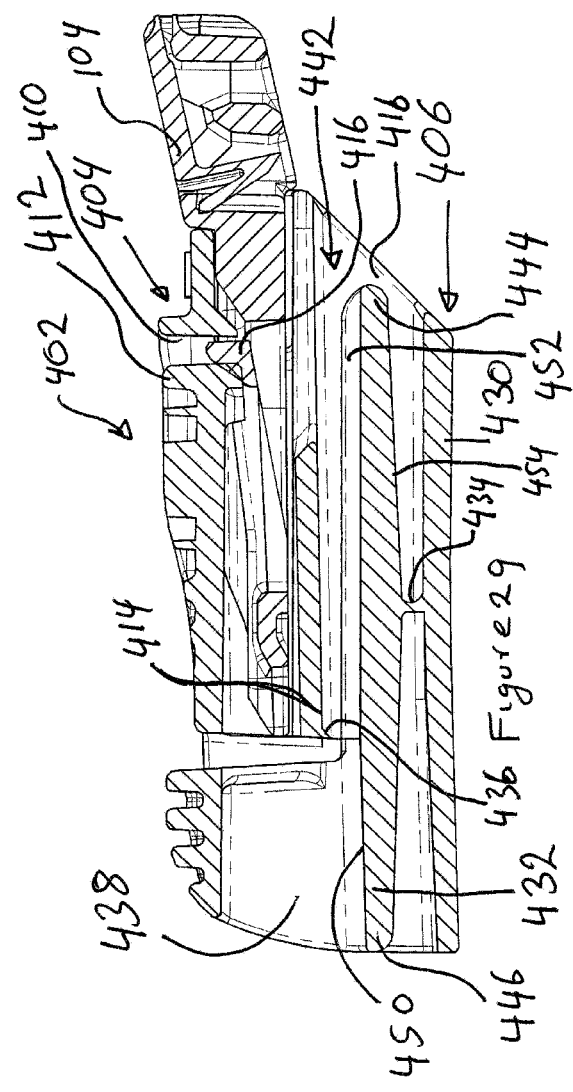
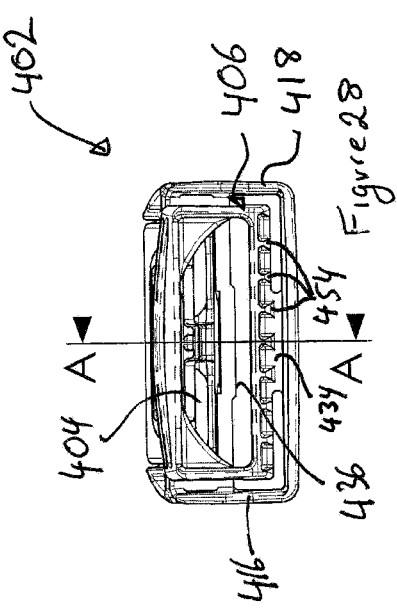

TOURNIQUET CLIP

FIELD OF INVENTION

This invention relates to clips for straps and more particularly to tourniquet clips but is not limited to tourniquet clips.

BACKGROUND

When taking blood a single use tourniquet assembly is used, that includes a tourniquet strap that is looped around a patient's limb, usually their arm. The tourniquet strap is tightened by engaging two tourniquet clip assemblies located along the tourniquet. Typically a male assembly is releasably inserted into a female assembly. When finished the user activates a release mechanism that allows the male assembly to be removed from the female assembly. The release mechanism typically includes a release button on the female assembly which allows for release using a single finger or hand.

Current tourniquet clips have the male and female assemblies each formed from multiple separate parts that need to be manufactured separately and then assembled.

It is desirable to provide a tourniquet clip that has a lower part count and accordingly a lower cost than existing tourniquet clips.

SUMMARY OF THE INVENTION

In one broad form embodiments of the present invention provide a clip adapted for use with an elongate strap for forming a tourniquet, the clip including first and second parts adapted to be connected to the strap, the first and second parts adapted to be releasably connected together, the first part adapted to be secured to the strap at a first location on the elongate strap;

a second part adapted to be mounted on the strap away from the first location whereby when the first and second parts are connected together the strap and the first and second parts form a closed loop;

the second part having a passageway adapted to have the strap pass therethrough between first and second ends of the passageway, whereby the distance of the second part from the first location is variable;

at least part of the passageway defined by first and second portions of the second part;

the second part including a strap grip adapted to, in use, releasably grip the strap;

the strap grip comprising a first and second grip portions movable relative to each other to vary the separation between at least parts of the first and second grip portions to enable gripped of the strap between the first and second grip portions;

wherein the first and second grip portion are integrally formed.

In another broad form embodiments of the present invention provide a tourniquet assembly comprising an elongate strap and a clip including first and second parts connected or mounted to the strap, the first and second parts adapted to be releasably connected together, the first part adapted to be secured to the strap at a first location on the elongate strap;

a second part adapted to be mounted on the strap away from the first location whereby when the first and second parts are connected together the strap and the first and second parts form a closed loop;

the second part having a passageway adapted to have the strap pass therethrough between first and second ends of the passageway, whereby the distance of the second part from the first location is variable;

at least part of the passageway defined by first and second portions of the second part;

the second part including a strap grip adapted to, in use, releasably grip the strap;

the strap grip comprising a first and second grip portions movable relative to each other to vary the separation between at least parts of the first and second grip portions to enable gripped of the strap between the first and second grip portions;

wherein the first and second grip portion are integrally formed.

The following features relate to both the clip and the tourniquet assembly embodiments of the invention.

The second grip portion may pivot or rock about an axis relative to the first grip portion.

The second grip portion may be elongate and pivot or rock about a transversely extending axis intermediate first and second longitudinal ends of the second grip portion.

The second grip portion may be connected to at least one support member.

The at least one support member may include at least one lower support member and the second grip portion may be located between the first portion and the at least one lower support member.

The at least one lower support member may be connected to the second grip portion by at least one transversely extending support wall or post.

The at least one support member may include two spaced apart side members extending either side of at least part of the second grip portion.

At least one of the at least one lower support member may extend between the side members.

The at least one of the at least one lower support member may be integrally formed with at least one of the side members.

The second grip portion may be connected to the side members. The second grip portion may be connected directly to the side members rather than to a lower support member.

The second portion may comprise the second grip portion.

The second portion may comprise a second wall. The second wall may extend longitudinally at least partially between the first and second ends.

The first portion may comprise the first grip portion.

The first portion may comprise a first wall. The first wall may extend longitudinally at least partially between the first and second ends.

The second portion may have a central surface region facing the first portion.

The second portion may have longitudinally extending side walls either side of the central surface region, the side walls extending toward the first portion.

The second part may comprises a first elongate wall and a second elongate wall, two spaced apart elongate side walls extending from the first elongate wall and a third elongate wall extending between the two side walls, the second wall located between the first and third walls and mounted on a transverse support wall intermediate the ends of the second wall for rotation about a transverse axis, the first and second walls defining at least part of the passageway and one end portion of the second wall comprising the second grip portion.

In another broad form embodiments of the present invention provide a tourniquet clip including a female part and a male part, the female part having adapted to receive the male part and releasably secure the male part, the female part having a release member adapted to be operated by a single finger to release the male part from engagement with the female part, wherein at least one and preferably both of the male and female parts are each a single, integrally formed, part.

The tourniquet clip is preferably adapted to have one of the male and female parts mountable upon a tourniquet strap and relocatable along the tourniquet strap. Preferably the respective part includes a tourniquet strap grip portion for gripping the tourniquet strap. Preferably the tourniquet strap grip portion is formed integrally with the respective clip part.

In preferred embodiments the tourniquet strap grip portion includes an elongate passageway through which the tourniquet strap passes.

The elongate passageway may be defined by a first wall and a movable second wall that extends alongside the first wall. The second wall is movable relative to the so first wall so that the strap is gripped between the first and second walls. Movement is preferably by a pivoting or rocking motion.

The second wall may be connected to at least one support member. When connected to at least one support member, movement is preferably by a pivoting or rocking motion relative to the at least one support member.

The second wall may be located between the first wall and the at least one support member.

In one form wall(s) or post(s) extend from the first wall and the at least one support member is on or connected to at least one of the wall(s) or post(s). The at least one support member may extend between wall(s) or post(s) extending from the first wall and spaced transversely. In one form the at least one support member is formed integrally with the wall(s) or post(s). In another form the at least one support member is formed integrally with one set of wall(s) or post(s) extending from the first wall about an integrated hinge and is rotatable about the hinge to engage with a second set of wall(s) or post(s) extending from the first wall transversely relative to the first set.

In preferred forms the each set of wall(s) or post(s) extending from the first wall is a single wall.

The second wall may be formed integrally with the support member. The second wall may be connected to the support member by at least one post or wall.

The support member may include a third wall.

In preferred forms the strap grip portion includes a first wall, two side walls extending from or adjacent longitudinally extending sides or edges of the first wall and a third wall extends between the side walls. The third wall is connected to the second wall intermediate the ends of the third wall by a transversely extending support wall, about which the third wall pivots or rocks.

In preferred embodiments the female part includes a recess to receive at least part of the male part, the male part including at least one latch member that engages the female part to retain the at least part of the male part in the female part. In preferred embodiments the female part includes an integrally formed release member that is movable to release the at least one latch member. In preferred embodiments the integrally formed release member includes an arm or leg cantilevered from the remained of the female part.

In preferred embodiments the female part includes the tourniquet strap grip portion.

BRIEF DESCRIPTION OF THE DRAWINGS

FIG. 3 is an exploded perspective view from above of the tourniquet clip of FIG. 1.

FIG. 4 is an exploded perspective view from below of the tourniquet clip of FIG. 1.

FIG. 5 is a perspective view from above and the front of the male part of the tourniquet clip of FIG. 1.

FIG. 6 is a perspective view from above and the front of the male part.

FIG. 7 is a plan view from above of the male part.

FIG. 8 is a side view of the male part.

FIG. 13 A to D are a cross sectional side views showing the engagement of the male and female parts.

FIG. 14 A to D are a cross sectional side views showing the disengagement of the male and female parts.

FIG. 15 is a cross sectional side view of a female part of a tourniquet clip according to a second embodiment of the invention.

FIG. 16 is an end view of the female part of FIG. 15.

FIG. 16A is a detail view of an alternate arrangement of the junction circled and labelled A in FIG. 16.

FIG. 17 is a plan view from above of the female part of FIG. 15 in the as manufactured state.

FIG. 18 is a plan view from below of the female part of FIG. 15 in the as manufactured state.

FIG. 28 is an end view of tourniquet clip according to a fourth embodiment of the invention.

FIG. 29 is a cross sectional side view of the tourniquet clip of FIG. 28 taken along line AA of FIG. 28.

DETAILED DESCRIPTION OF PREFERRED AND OTHER EMBODIMENTS

Figure 1:
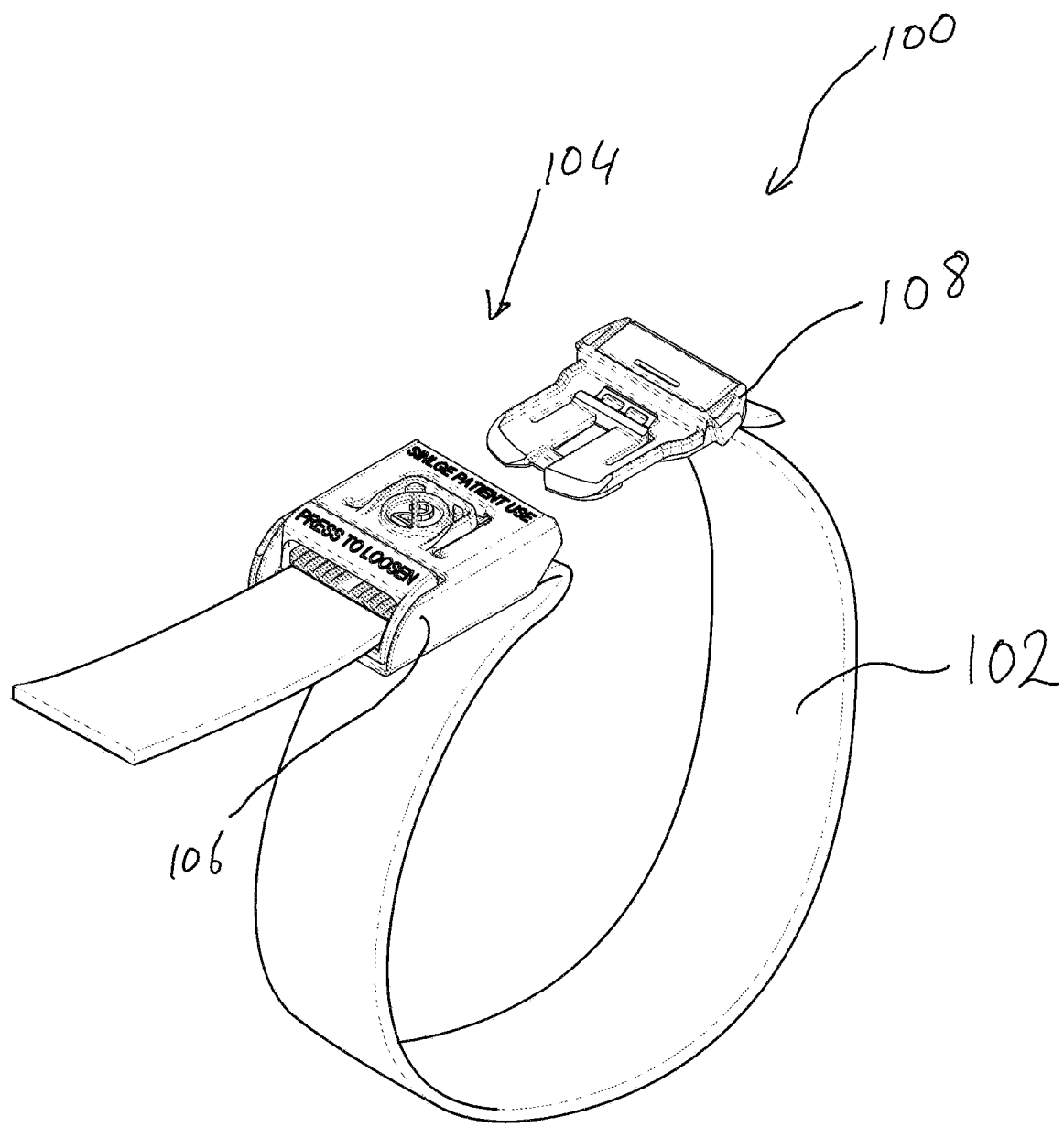
FIG. 1 is an exploded perspective view from above of a tourniquet assembly with a tourniquet clip according to a first embodiment of the invention.
Figure 2:
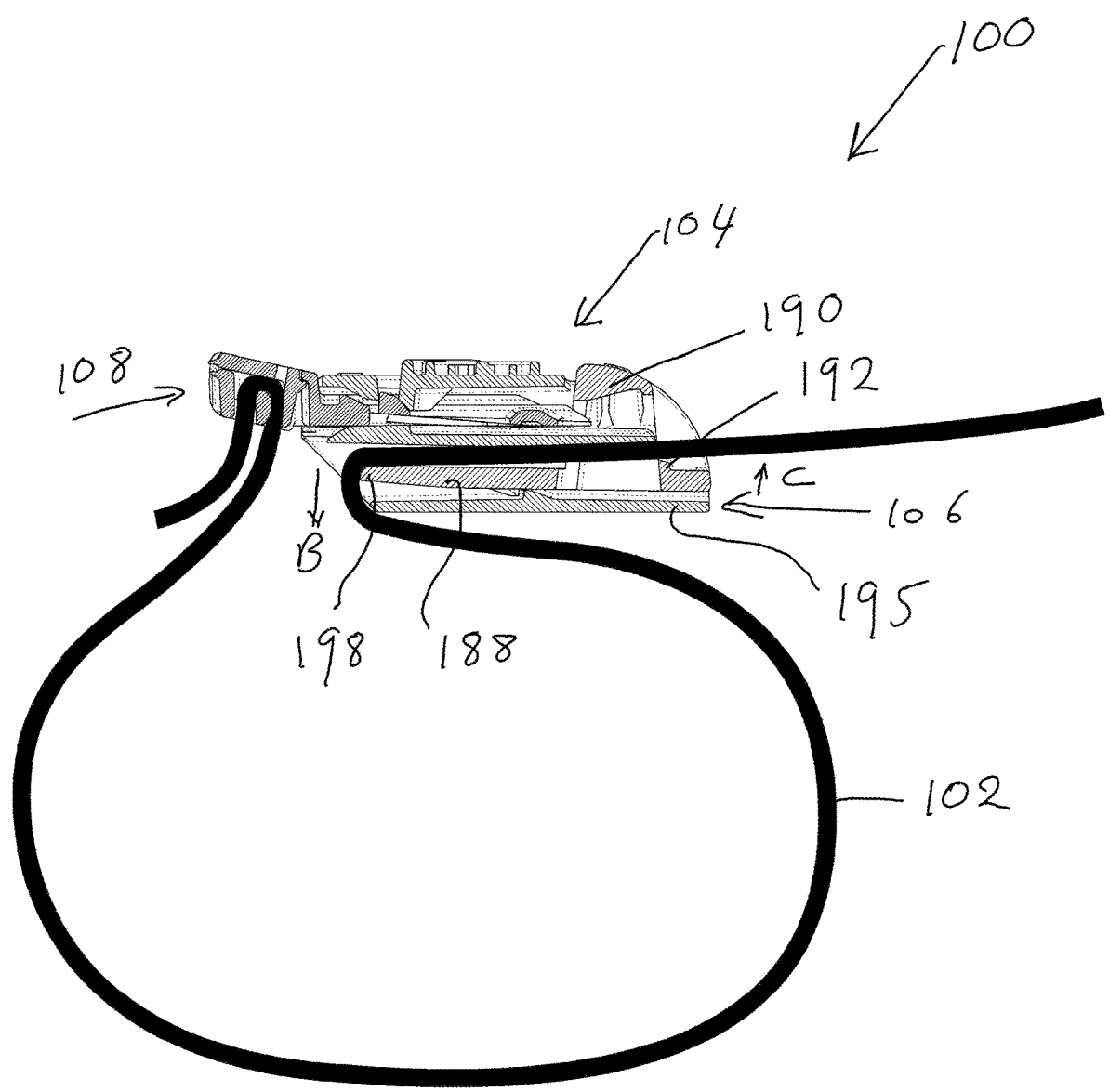
FIG. 2 is a side cross sectional view of a tourniquet assembly of FIG. 1.

Referring to FIGS. 1 to 14 there is shown a tourniquet assembly 100 with a tourniquet clip according to a first embodiment of the invention. The tourniquet assembly 100 includes a strap 102 and a tourniquet clip 104, itself including a female part 106 and a male part 108. The strap 102 is preferably elastic.

The male part 108 is intended to be located near one end of the tourniquet strap 102 in a fixed position (once the tourniquet assembly 100 has been assembled).

The female part 106 serves two functions, one being to engage with the male part 104 in a releasable manner to form a closed loop with the strap 102 and the other to allow the strap 102 to be moved through the female part 106, so as to change the size of the loop so formed. More particularly, the female part 104 is intended to be easily movable along the strap 102 toward the male part 108 whilst movement away is prevented or resisted, unless allowed by the user. Accordingly, the female part has a male retaining portion and a strap grip portion.

The male part 108 has a tongue 110 that has forward end 112. Forward end 112 is provided with angled face 114 to aid insertion of tongue 112 into female assembly 106. Tongue 110 includes latch member 116 that is cantilevered from near the front end 112 and extends rearwards. Latch member 116 is upturned at its rearward end 118 and has angled face 120.

The rearward end 118 of latch member 116 may deflect up and down relative to the tongue 110.

In this first embodiment latch member 116 can be considered to be two spaced apart rearward extending arms 122 joined at the rearwards end 118 by cross arm 124. Similarly the tongue 110 can be considered to be two forward extending arms 126 joined by cross arm 128. Latch member 116 may be formed of a single arm or of more than two arms. Cross arm 124 need not be a different cross sectional shape to arms 126.

The male part 108 has strap retention portion 130 that includes two openings 132, 134, separated by transverse arm 136. Opening 132 is delineated by transverse arm 136 and cross member 138. Opening 134 is delineated by transverse arm 136 and rear cross member 139.

Figure 9:
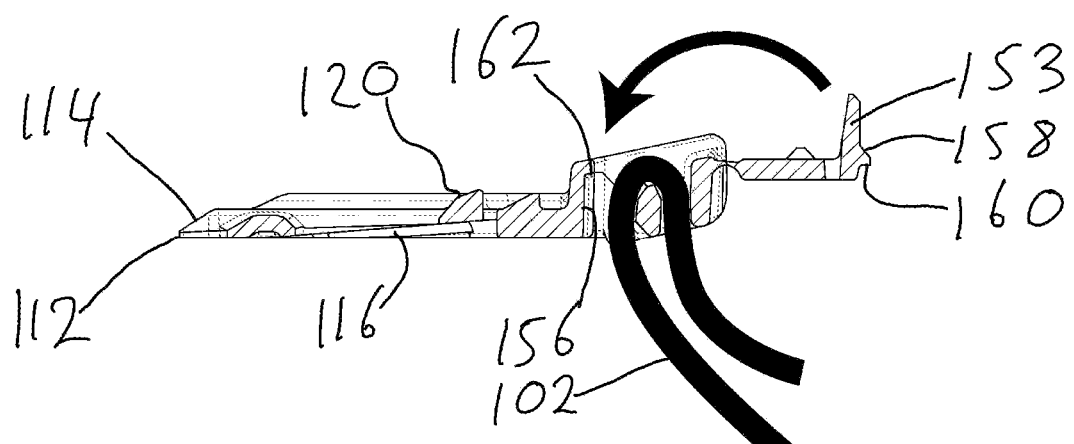
FIG. 9 is a cross sectional side view of the male part with the tourniquet strap engaged with but not secured in the male part.

The tourniquet strap 102 may be passed from below, though opening 132 and then downwards through opening 134, engaging the top of transverse arm 136, as seen in FIG. 9. The upper face of arm 136 includes a strap grip surface 141. In this embodiment the strap grip surface 141 includes a series of retaining protrusions 142 to engage the underside of tourniquet strap 102. The configuration of grip surface 141 and the shape and number of the protrusions 142 is not critical and may be modified. Protrusions 142 may be omitted if desired.

Integrally formed with the male part is strap retainer 144. Strap retainer 144 is connected to the rear of cross member 139 about hinge line 146. Strap retainer 144 includes first strap grip surface 148, which includes recesses 150 sized and positioned to cooperate with protrusions 142. Strap retainer 144 also includes second strap grip surface 152 on wall 153. The strap retainer 144 may be rotated about hinge 146 so that first strap grip surface 148 extends over the transverse arm 136 with wall 153 extending into opening 132. Wall 153 includes protrusion 154 that engages with recess 156 in cross member 139 to hold the strap retainer 144 in the closed position. Protrusion 154 is preferably a snap fit into recess 156, with angled face 158 to assist closure and faces 160, 162 extending generally radially so as to resist opening.

Figure 10:
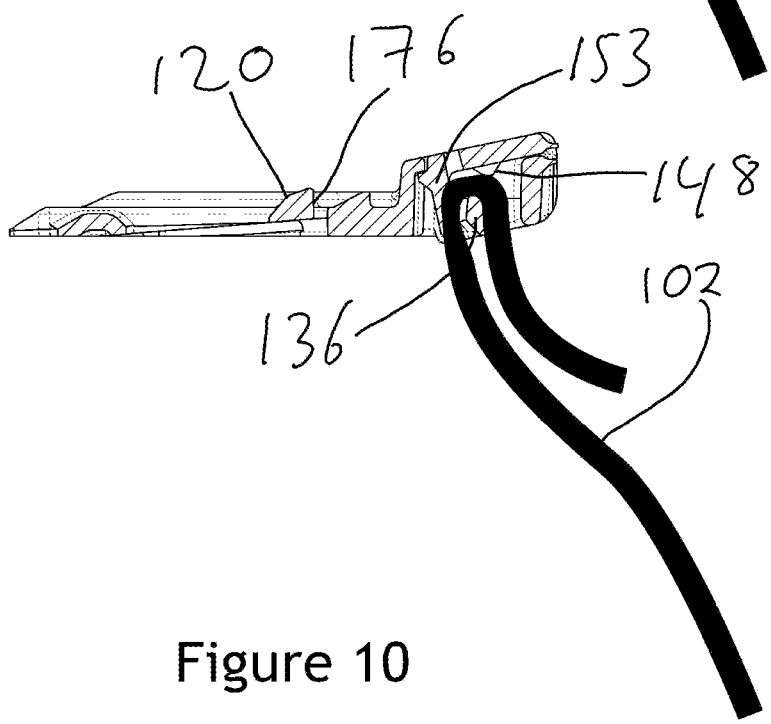
FIG. 10 is a cross sectional side view of the male part with the tourniquet strap engaged with and secured in the male part.
Figure 11:
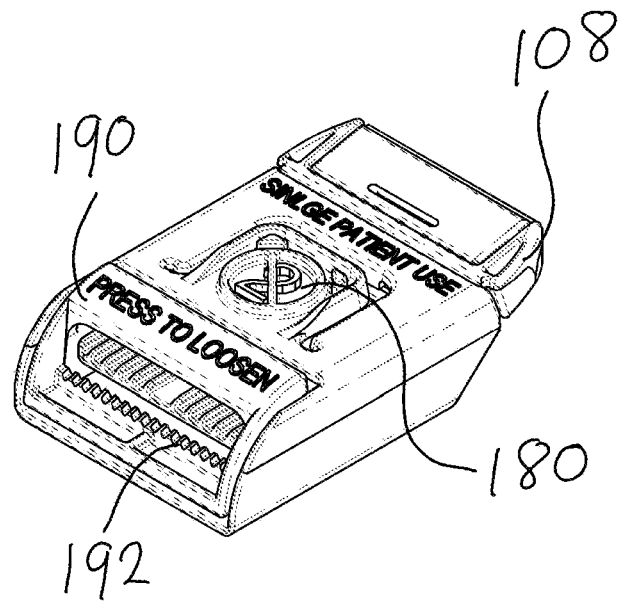
FIG. 11 is a perspective view from above of the male and female parts engaged together. For clarity the tourniquet strap is omitted.
Figure 12:
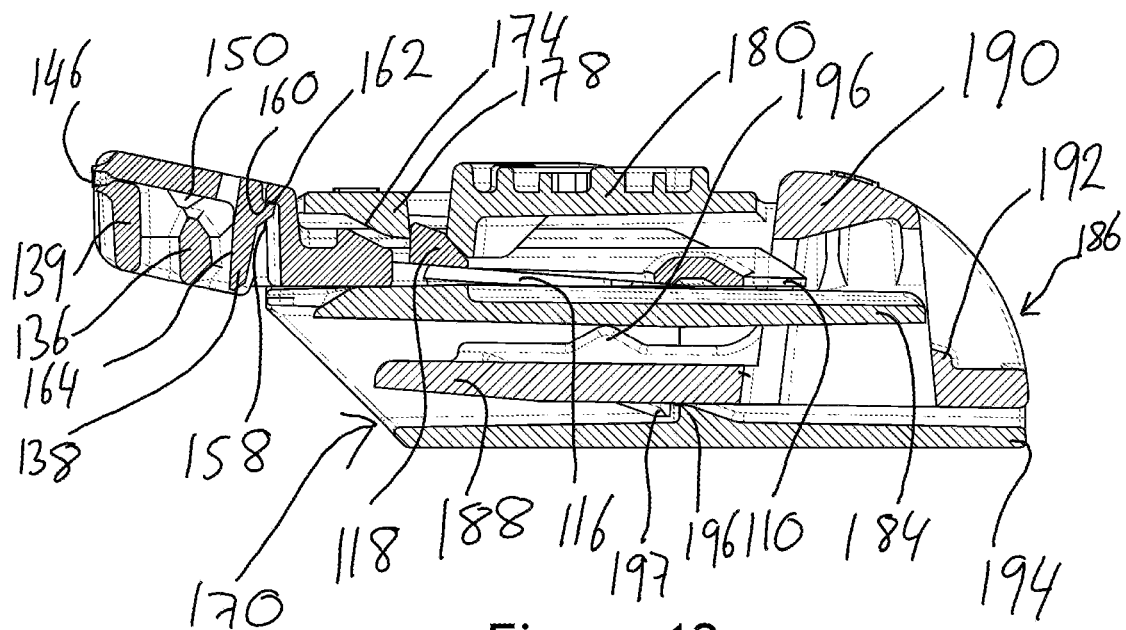
FIG. 12 is a cross sectional side view of the male and female parts engaged together. For clarity the tourniquet strap is omitted.
Figure 19:
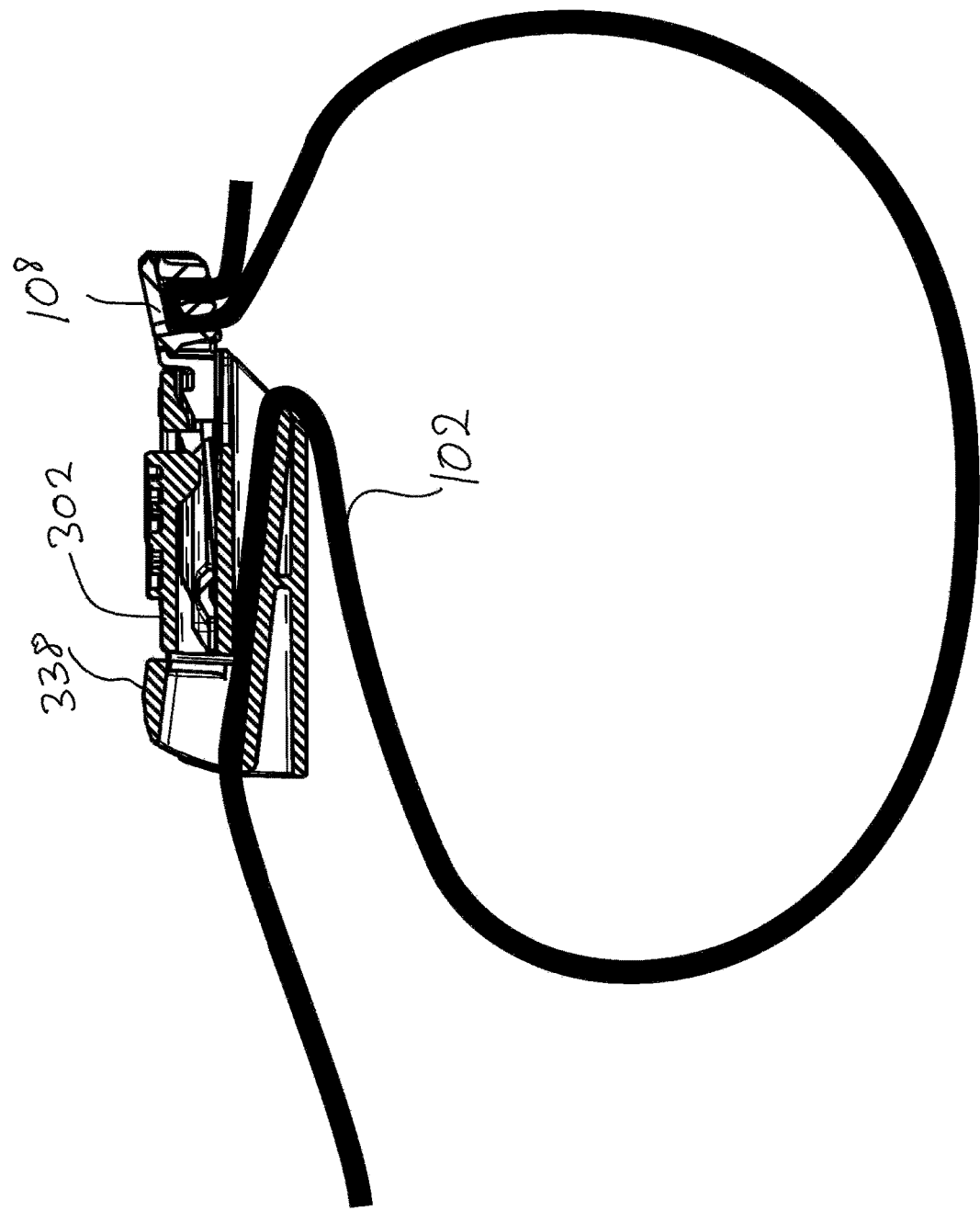
FIG. 19 is a side cross sectional view of a tourniquet assembly with a tourniquet clip according to a third embodiment of the invention.
Figure 21:
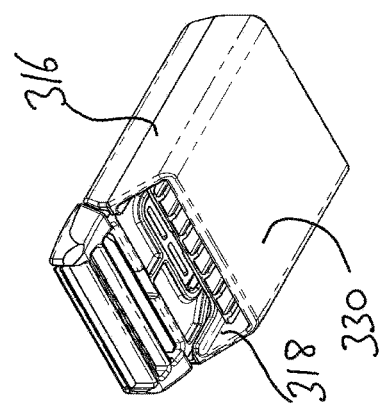
FIG. 21 is a perspective view from below of the tourniquet clip of FIG. 19.
Figure 20:
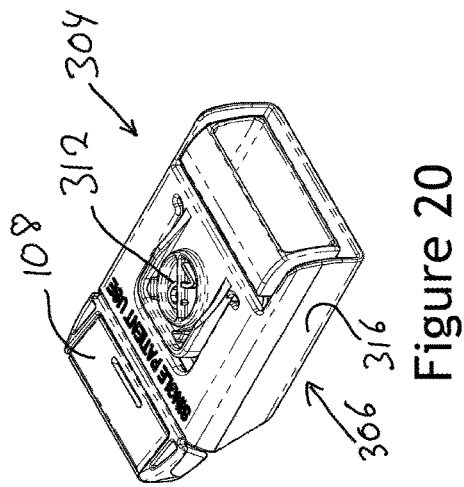
FIG. 20 is a perspective view from above of the tourniquet clip of FIG. 19.
Figure 25:
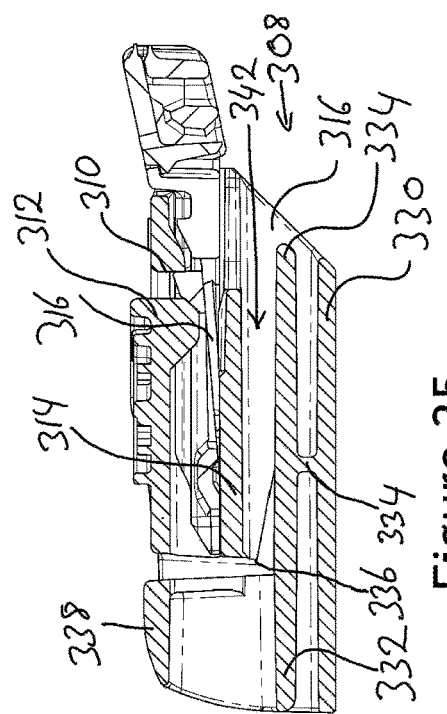
FIG. 25 is a cross sectional side view of tourniquet clip of FIG. 19 taken along line AA of FIG. 24.
Figure 24:
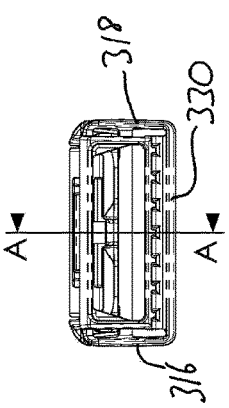
FIG. 24 is an end view of the tourniquet clip of FIG. 19.
Figure 22:
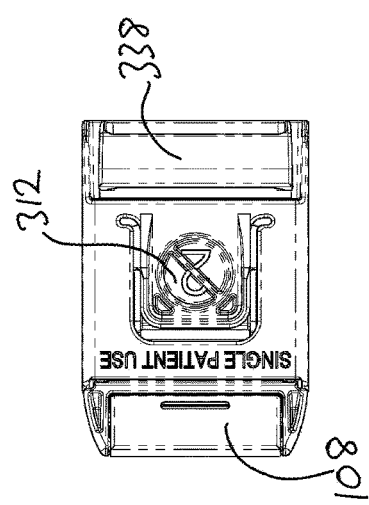
FIG. 22 is a plan view from above of the tourniquet clip of FIG. 19.
Figure 23:
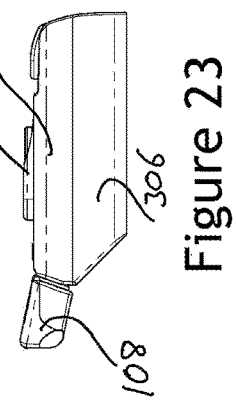
FIG. 23 is a side view of the tourniquet clip of FIG. 19.
Figure 26:
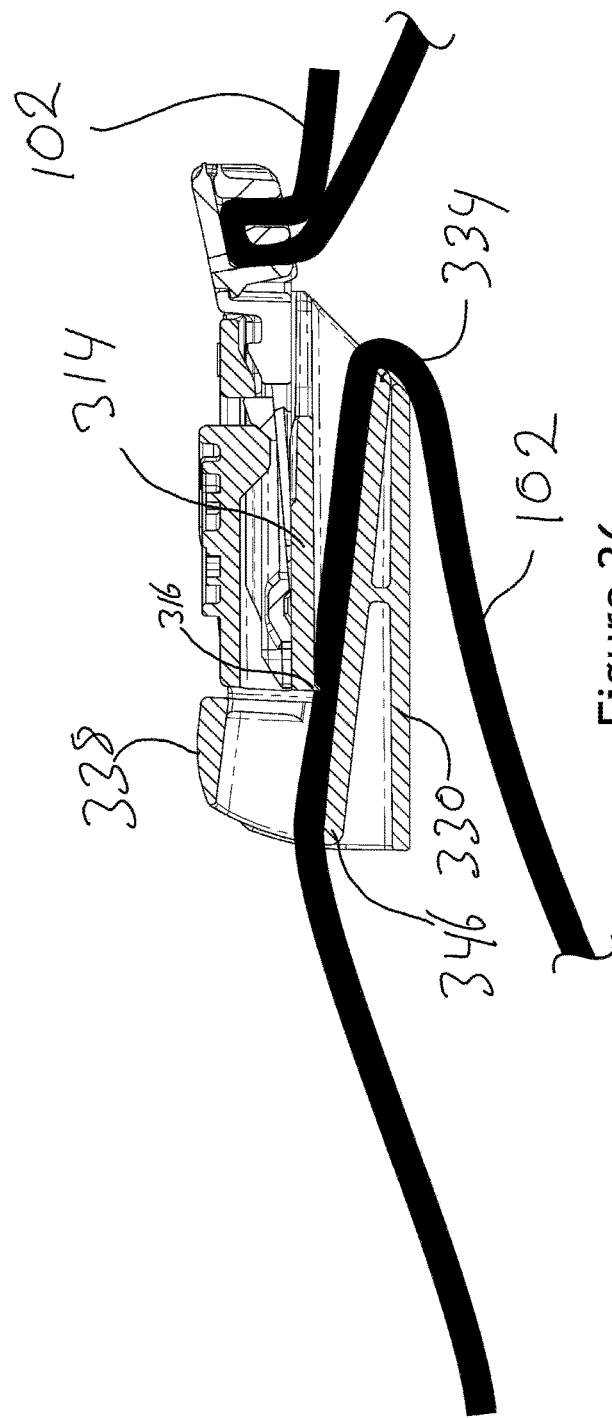
FIG. 26 is a side cross sectional view of a tourniquet assembly of FIG. 19 with the assembly in use and the tourniquet strap gripped by the strap grip of the clip.
Figure 27:
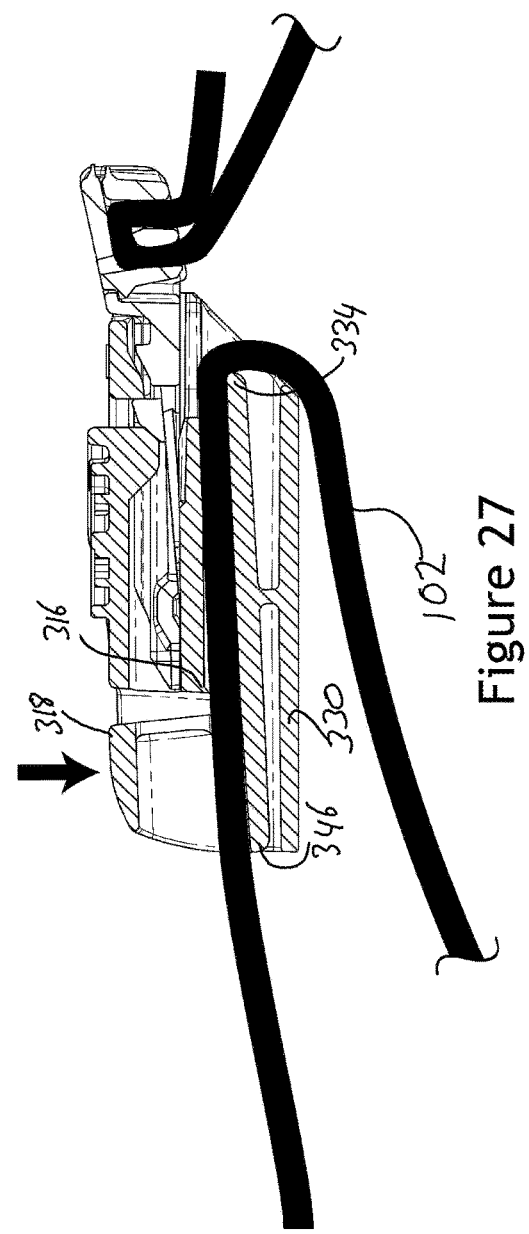
FIG. 27 is a side cross sectional view of a tourniquet assembly of FIG. 19 with the assembly in use and but with the tourniquet strap grip in a release position.

As best seen in FIG. 10, when the strap retainer 144 is closed strap 102 is trapped between cross arm 136 and first strap grip surface 148. The gap between the surface 148 and protrusions 142 is preferably such that the strap distorts around protrusions 142. The wall 153 passes into opening 132 and, as seen in FIG. 10, the gap between second strap grip surface 152 and cross arm 136 is less than the thickness of the strap, so that the wall 153 is bent slightly or angled forward so as to apply a compressive load to the strap via second strap grip surface 152.

Thus a single moulding provides a male tongue and a strap retention mechanism.

Female part 106 includes housing 140 which is adapted to receive the tongues 110, 116 of male part 108, thought opening 172. Opening 172 is partially defined by lower wall 184 and cross member 178. The separation of lower wall 184 and cross member 178 is less than the maximum combined height of primary tongue 110 and latch member 116.

As the tongue 110 is inserted into the opening 172, angled face 120 of latch member 116 engages angled face 174 and the free end 118 deflects elastically downwards to pass through opening 172. Once the free end 118 of latch member 116 has passed through the opening 172 the latch member 116 springs back towards its un-deflected state, with face 176 overlapping cross member 178, so preventing removal. Removal requires that latch member 116 be deflected downwards to align with opening 172.

A release arm 180 is integrally formed with housing 140. The release arm 180 is cantilevered from the remainder of housing 140 and overlies the tongue 110. The release arm 180 includes angled face 182 that overlies the angled face 120 of male part 108.

The male and female parts 104, 106 may be configured so that when inserted the angled face 120 bears against face 182 and slightly deflects the release arm 180 upwards. Due to the angled nature of faces 120 and 182 this results in a small force urging the rear face 176 of latch member 116 against the cross member 178.

To release the male part 108 the user presses on the release arm 180, deflecting the latch member 116 downwards to align with opening 172. The angled faces 120 and 182 cause the male part 108 to move rearwards once the latch member 116 aligns into the opening 172. In use the strap 102 is tensioned and the tension in the strap 102 also pulls the male part 108 out of the female part 106. Although preferred, use of the tension in the strap 102 is not critical to separating of the parts.

Movement of the female part 106 along the strap 102 is achieved by providing a through passageway 170 through which the strap passes. A strap grip 186 is provided that releasably grips the strap 102 between itself and wall 184. In this embodiment the strap grip 186 is a separate component that has features of tongue 188, release member 190, strap engagement member 192. The strap grip 186 is inserted into the passageway 170 of housing 140 from end 194. Lower wall 195 includes wall 196 that cooperates with latches 197 and prevents or resists removal of the strap grip 186 from the housing 140. The tongue 188 also includes protrusions 196 that bear against wall 184 and act as a pivot points for strap grip 186 relative to the housing 140.

The strap 102 is passed through the passageway defined between the wall 184 tongues 188 and strap engagement member 192. The gap between the tongue 188 and wall 184 is preferably greater than the thickness of the strap 102. The gap between the strap engagement member 192 and wall 184 is smaller and in use, when the strap is tensioned the strap 102 is held between these two parts. The strap engagement member 192 may have a serrated edge to aid gripping of the strap 102. The strap grip 186 and housing 140 may be configured so that when not in tension about a patient's arm the strap 102 is lightly gripped by the strap grip 186 and may move relatively easily in both directions.

In use the strap is tensioned around the patient's arm, as in FIG. 1, and forms a U around the free end of the tongue 188. The tension in the strap 102 pulls the free end 198 of the tongue 188 towards wall 195, as indicated by arrow B in FIG. 1. Due to protrusion 196 bearing on wall 184 this urges strap engagement member 192 toward the wall 184, as indicated by arrow C in FIG. 1, so holding or increasing the hold on the strap 102.

To release the strap 102 the user pushes the release member 190 downwards causing the strap grip 186 to pivot about protrusion 196, so increasing the gap between strap engagement member 192 and wall 184 and releasing the strap.

Although the free end 198 of the tongue 188 rotates toward wall 184, because the gap between these two parts is greater than the thickness of the strap this reduction in size does not cause the strap 102 to be held or held to any significant extent. The tension in the strap thus pulls the strap 102 through the passageway 170 to reduce the tension. There may be a small amount of gripping of the strap between the tongue 188 and wall 184. However, the tension in the strap will overcome a minor amount of gripping.

FIGS. 15 to 19 schematically show a female part 202 according to a second embodiment of the invention. The female part 202 may be used with the male part 104 of the first embodiment.

The female part 202 is an integrally formed single component that includes a male retaining portion 204 for receiving the male part 104 and a strap grip portion 206 for gripping the strap 102.

The male retaining portion 204 is substantially the same as the retaining portion of the first embodiment and operates in the same manner. The male retaining portion 204 includes opening 208 for receiving the tongue, wall 210 against which latch member 116 engages against and release button 212 to depress latch member 116.

Strap grip portion 206 is formed integrally with female retaining portion 204. Two spaced part walls 216 and 218 extend downwards from wall 214. Strap grip portion 206 is formed integrally with and extends from the free end of wall 216 about hinge 228.

Strap grip portion 206 includes lower wall 230 and upper wall 232. Upper wall 232 is connected to lower wall 230 by posts 234 intermediate the ends of lower wall 230. Posts 234 are sized to allow the upper wall 232 to rock about the general area of posts 234. This may be by flexing or bending of the posts 234, as in this embodiment. As an alternative or in addition, one or both of the junctions of the posts 234 with walls 230 and 232 may be a hinge, as seen in FIG. 16A which shows an possible junction of the post 234 with wall 232. If desired the posts may be replaced by a series of posts extending transversely across walls 230, 234 or a transverse wall extending across walls 230, 234. Such a transverse wall may be continuous or discontinuous (e.g. two or more inline transverse walls).

Upper wall 232 includes strap grip wall 236 and release member 238. In contrast to the first embodiment the release member 238 is located at the end of the strap grip portion 206.

In the as manufactured state female part is in a generally flat state. The strap grip portion 206 is rotated about hinge 228 so that lower wall 230 is parallel to wall 214 and edge 240 engages with wall 218. In the embodiment shown the wall 218 has a ledge 222 on which the edge 240 rests, although a grove running along the wall 218 may be provided. Use of a groove assists in limiting flexing of lower wall 230 Wall 218 may be provided with angled face 224 to assist movement of the grip portion during assembly. Wall 218 may flexes sideways to allow wall 230 to pass and then snap back to its un-deflected state.

Because there is no closed passageway, assembly can take the step of laying the strap 102 upon the wall 214, between walls 216 and 218, and then rotating the strap grip portion 206 to the closed position to secure the female part 202 to the strap 102.

Strap grip wall 236 is adjacent wall 214 and provides a gap 242 through which strap 102 may pass. Release member 238 extends at the end of male retaining portion 204.

The strap grip portion 206 operates the same as the strap engagement member 192 of the first embodiment, in that tension in the strap 102 rotates wall 232 about posts 234, urging the end 244 of upper wall 232 toward lower wall 230 and strap grip wall 236 toward wall 214, trapping strap 102. Release is achieved by pressing down on release member 238.

Thus the female part 202 provides a unitary component. Further, the female part 202 allows assembly of a tourniquet assembly without needing to thread the tourniquet strap through a passageway.

FIGS. 20 to 28 schematically show a female part 302 according to a third embodiment of the invention. The female part 302 may be used with the male part 104 of the first embodiment.

As with the other embodiments the female part has a male retaining portion 304 and a strap grip portion 306. In this embodiment the male retaining portion 304 and the strap grip portion 306 are formed integrally and without the need for post manufacturing assembly.

The male retaining portion 304 is substantially the same as the retaining portion of the first embodiment and operates in the same manner. The male retaining portion 304 includes opening 308 for receiving the tongue, wall 310 against which latch member 116 engages against and release button 312 to depress latch member 116.

Strap grip portion 306 is formed integrally with male retaining portion 304. Two spaced part walls 316 and 318 extend downwards from wall 314.

Strap grip portion 306 includes lower wall 330 and upper wall 332. Lower wall 330 extends between walls 316 and 318. Upper wall 332 is connected to lower wall 330 by transverse wall 334 intermediate the ends of lower wall 330. Transverse wall 334 is sized to allow the upper wall 332 to rock about the transverse wall 334. This may be by flexing or bending of the transverse wall 334, as in this embodiment. As an alternative or in addition, one or both of the junctions of the transverse wall 334 with walls 330 and 332 may be a hinge.

The transverse wall 334 may be continuous or discontinuous (e.g. two or more inline transverse walls). If desired the transverse wall may be replaced by one or more posts.

Upper wall 332 includes release member 338, located at the end of wall 332. The wall 332 does not include a strap grip and instead wall 314 includes downward extending strap grip 336. This is for manufacturing purposes and, if desired, the strap grip 336 may be located on the wall 332.

Thus there is passageway 342 between walls 314 and 332 through which the strap 102 may pass.

The strap grip portion 306 operates the same as the strap engagement member 192 of the first embodiment and strap grip portion 206 of the second embodiment, in that tension in the strap 102 rotates wall 332 about transverse wall 334, urging the end 344 of upper wall 332 downwards toward lower wall 330 and the other end 346 upwards, trapping strap 102 between wall 332 and strap grip 336. Release is achieved by pressing down on release member 338 which rotates the wall 332 in the opposite direction so that the strap 102 is released from the grip of the strap grip 336.

Thus the female part 302 provides a unitary component.

Figure 30:
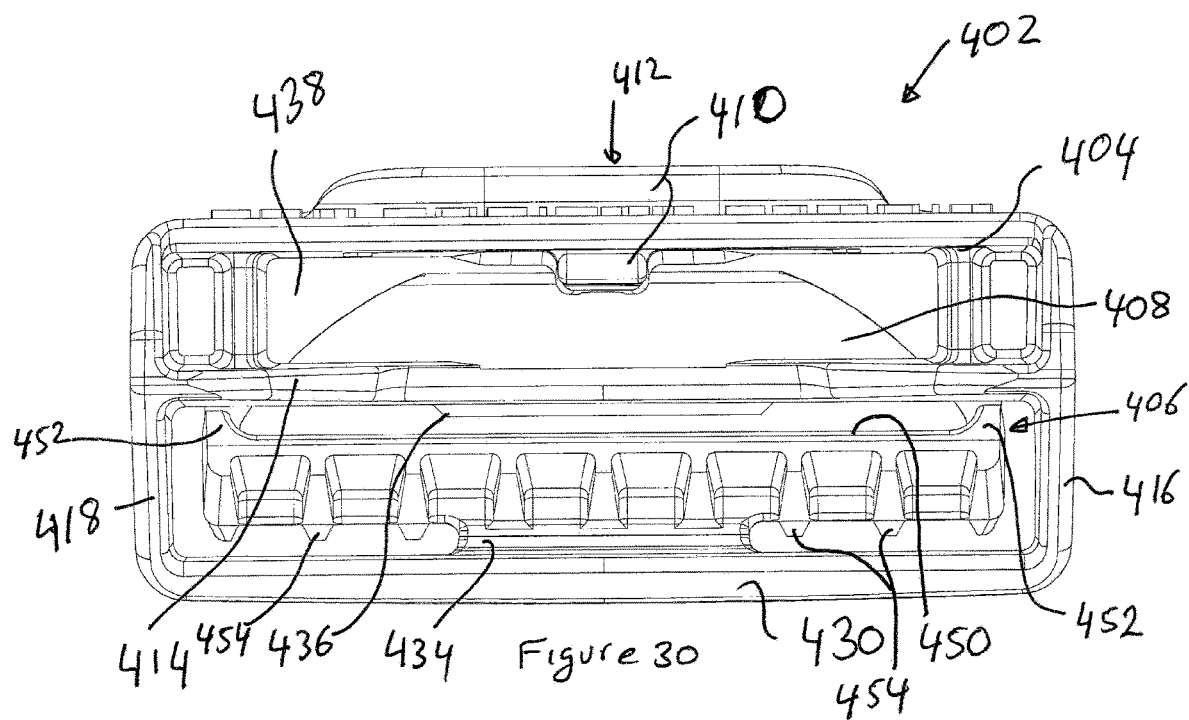
FIG. 30 is an opposite end view of the tourniquet clip of FIG. 28.

FIGS. 28 to 30 schematically show a female part 402 according to a fourth embodiment of the invention. The female part 402 may be used with the male part 104 of the first embodiment.

As with the other embodiments the female part has a male retaining portion 404 and a strap grip portion 406. In this embodiment the male retaining portion 404 and the strap grip portion 406 are formed integrally and without the need for post manufacturing assembly.

The male retaining portion 404 is substantially the same as the retaining portion of the first embodiment and operates in the same manner. The male retaining portion 404 includes opening 408 for receiving the tongue, wall 410 against which latch member 116 engages against and release button 412 to depress latch member 116.

Strap grip portion 406 is formed integrally with male retaining portion 404. Two spaced part walls 416 and 418 extend downwards from wall 414.

Strap grip portion 406 includes lower wall 430 and upper wall 432. Thus there is passageway 442 between walls 414 and 432 through which the strap 102 may pass.

Lower wall 430 extends between walls 416 and 418. Upper wall 432 is connected to lower wall 430 by transverse wall 434 intermediate the ends of lower wall 430. Transverse wall 434 is sized to allow the upper wall 432 to rock about the transverse wall 434. This may be by flexing or bending of the transverse wall 434, as in this embodiment. As best seen in FIG. 30, transverse wall 434 does not extend across the full width of upper wall 432. As an alternative or in addition, one or both of the junctions of the transverse wall 434 with walls 430 and 432 may be a hinge.

The transverse wall 434 may be continuous or discontinuous (e.g. two or more inline transverse walls). If desired the transverse wall may be replaced by one or more posts.

Upper wall 432 includes release member 438, located at the end of wall 432. The underside of the upper wall 432 includes ribs 454

The wall 414 includes downward extending strap grip 436. The strap grip 436 does not extend the full with of the wall 436.

If desired, the strap grip 436 may be located on the wall 432. However, it does allow the upper surface 450 of wall 432 to be generally smooth (and preferably planar) in the longitudinal direction, as best seen in FIG. 29. This allows the strap to more easily slide relative to wall 432 compared to the situation where the strap grip 436 is located on the wall 432. The wall 432 is provided with side walls 452 that serve to retain the strap 102 centred and prevent the strap sliding into the gaps between the upper wall 432 and side walls 416 and 418.

The Central Portion

The strap grip portion 406 operates the same as the strap engagement member 192 of the first embodiment, strap grip portion 206 of the second embodiment and strap grip portion 306 of the third embodiment, in that tension in the strap 102 rotates wall 432 about transverse wall 434, urging the end 444 of upper wall 432 downwards toward lower wall 430 and the other end 446 upwards, trapping strap 102 between wall 432 and strap grip 436. Release is achieved by pressing down on release member 438 which rotates the wall 432 in the opposite direction so that the strap 102 is released from the grip of the strap grip 436.

Thus the female part 402 provides a unitary component.

Whilst the embodiments shown have the mechanism for adjusting the effective strap length as part of or mounted on or in the female part, the mechanism for adjusting the effective strap length may be part of or mounted on or in the male part. Further, whilst male/female parts are preferred other mechanisms may be used for connecting the two clip parts together In the embodiments shown the female parts have lower walls 195, 230, 330 and 430. These walls are continuous and extend generally the full length of the female parts.

Whilst lower walls 195, 230, 330 and 430 provide a surface against which a user can press when pressing on release buttons 180, 212, 312 and 412 or release members 190, 238, 338 and 438 and also act as a guard prevent a user easily accessing the walls 188, 232 and 332, the provision of one or more guards or one or more reaction surfaces is not critical to the invention, although preferred. The parts may be modified to have other structures that provide one or more guards or one or more reaction surfaces, including but not limited to a lower wall with apertures therethrough or a series of transverse walls spaced longitudinally along the relevant part or longitudinally extending walls spaced transversely across the relevant part.

These lower walls 195, 230, 330 and 430 provide a small central section against which the walls 188, 232, 332 and 432 engage or rock/pivot about and an end section to enable the strap to form a U about the forward end and, as such, do need not be continuous for the functioning of gripping the strap. For example, a bar or short wall may extend transversely underneath the forward end of the walls 188, 232, 332 and 432 so as to enable the strap to form a U about the forward end of the respective wall. Similarly a bar or short wall may extend transversely underneath the centre of the walls 188, 232, 332 and 432 to provide an engagement surface for wall 188 or a mounting area for walls 232, 332 and 432 to rock/pivot about. Similarly a bar or short wall may extend transversely underneath the respective release member to allow a user to press against when depressing the release members.

It will be appreciated that the features of one or more guards and one or more reaction surfaces are not dependent on each other and may be provided by separate structure(s). Similarly, structure(s) to secure and/or enable the motion of the walls 188, 232, 332 and 432 relative to the rest of the part may be provided that are separate from any structure(s) providing any guard(s) and/or any reaction surface(s).

Unless the context clearly requires otherwise, throughout the description and any claims the words "comprise", "comprising", and the like are to be construed in an inclusive sense as opposed to an exclusive or exhaustive sense; that is to say, in the sense of "including, but not limited to".

The features of the invention described or mentioned in this document may be combined in any combination of features where features are not mutually exclusive.

It will be apparent to those skilled in the art that many obvious modifications and variations may be made to the embodiments described herein without departing from the spirit or scope of the invention.

The claims defining the invention are as follows:

1. A clip adapted for use with an elongate strap for forming a tourniquet, the clip including first and second parts adapted to be connected to the strap, the first and second parts adapted to be releasably connected together,
the first part adapted to be secured to the strap at a first location on the elongate strap;
a second part adapted to be mounted on the strap away from the first location whereby when the first and second parts are connected together the strap and the first and second parts form a closed loop;
the second part having a passageway adapted to have the strap pass therethrough between first and second ends of the passageway, whereby the distance of the second part from the first location is variable;
at least part of the passageway defined by first and second portions of the second part;
the second part including a strap grip adapted to, in use, releasably grip the strap;
the strap grip comprising a first and second grip portions movable relative to each other to vary the separation between at least parts of the first and second grip portions to enable gripped of the strap between the first and second grip portions;
wherein the first and second grip portions are integrally formed.

2. The tourniquet clip as claimed in claim 1 wherein the second grip portion pivots or rocks about an axis relative to the first grip portion.

3. The tourniquet clip as claimed in claim 1 wherein the second grip portion is elongate and pivots or rocks about a transversely extending axis intermediate first and second longitudinal ends of the second grip portion.

4. The tourniquet clip as claimed in claim 1 wherein the second grip portion is connected to at least one support member.

5. The tourniquet clip as claimed in claim 4 wherein the at least one support member includes two spaced apart side members extending either side of at least part of the second grip portion.

6. The tourniquet clip as claimed in claim 5 wherein the at least one support member includes at least one lower support member and wherein the second grip portion is located between the first portion and the at least one lower support member.

7. The tourniquet clip as claimed in claim 6 wherein at least one lower support member is integrally formed and connected to the second grip portion by at least one transversely extending support wall or post.

8. The tourniquet clip as claimed in claim 7 wherein at least one of the at least one lower support member extends between the side members.

9. The tourniquet clip as claimed in claim 1 wherein at least one of the at least one lower support member is integrally formed with at least one of the side members.

10. The tourniquet clip as claimed in claim 9 wherein the second grip portion is connected to the side members.

11. The tourniquet clip as claimed in claim 10 wherein the second portion comprises the second grip portion.

12. The tourniquet clip as claimed in claim 11 wherein the second portion comprises a second wall.

13. The tourniquet clip as claimed in claim 12 wherein the first portion comprises the first grip portion.

14. The tourniquet clip as claimed in claim 13 wherein the first portion comprises a first wall.

15. The tourniquet clip as claimed in claim 14 wherein the second portion has a central surface region facing the first portion.

16. The tourniquet clip as claimed in claim 15 wherein the second portion has longitudinally extending side walls either side of the central surface region, the side walls extending toward the first portion.

17. The tourniquet clip as claimed in claim 1 wherein the second part comprises a first elongate wall and a second elongate wall, two spaced apart elongate side walls extending from sides of the first elongate wall and a third elongate wall extending between the two side walls, the second wall located between the first and third walls and mounted on a transverse support wall intermediate the ends of the second wall for rotation about a transverse axis, the first and second walls defining at least part of the passageway and one end portion of the second wall comprising the second grip portion, the first, second, third and support walls being integrally formed.

18. A tourniquet assembly comprising an elongate strap and a clip including first and second parts connected or mounted to the strap, the first and second parts adapted to be releasably connected together,
the first part adapted to be secured to the strap at a first location on the elongate strap;
a second part adapted to be mounted on the strap away from the first location whereby when the first and second parts are connected together the strap and the first and second parts form a closed loop;
the second part having a passageway adapted to have the strap pass therethrough between first and second ends of the passageway, whereby the distance of the second part from the first location is variable;
at least part of the passageway defined by first and second portions of the second part;
the second part including a strap grip adapted to, in use, releasably grip the strap;
the strap grip comprising a first and second grip portions movable relative to each other to vary the separation between at least parts of the first and second grip portions to enable gripped of the strap between the first and second grip portions;
wherein the first and second grip portions are integrally formed.

19. The tourniquet as claimed in claim 18 wherein the second part comprises a first elongate wall and a second elongate wall, two spaced apart elongate side walls extending from the first elongate wall and a third elongate wall extending between the two side walls, the second wall located between the first and third walls and mounted on a transverse support wall intermediate the ends of the second wall for rotation about a transverse axis, the first and second walls defining at least part of the passageway, a portion of the second wall comprising the second grip portion and a portion of the first wall comprising the first grip portion, the first, second, third and support walls being integrally formed.

20. The tourniquet as claimed in claim 19 wherein the second elongate wall has a central surface region facing the first elongate wall and longitudinally extending side walls either side of the central surface region, the side walls extending toward the first elongate wall.

* * * * *